United States Patent [19]

Hawn et al.

[11] 4,330,298

[45] May 18, 1982

[54] REDUCTIVE PYROLYSIS METHOD FOR DETERMINING TRACE SULFUR

[75] Inventors: David D. Hawn; Robert E. Reim, both of Midland, Mich.

[73] Assignee: The Dow Chemical Company, Midland, Mich.

[21] Appl. No.: 192,584

[22] Filed: Sep. 30, 1980

[51] Int. Cl.$^3$ .............................................. G01N 27/46
[52] U.S. Cl. ............................... 23/230 PC; 204/1 T; 422/80
[58] Field of Search ........................ 23/230 PC, 232 E; 422/90, 98, 78, 80; 204/195 H, 1 F

[56] References Cited

U.S. PATENT DOCUMENTS

| | | | |
|---|---|---|---|
| 3,304,243 | 2/1967 | Capuano | 204/1 F |
| 3,410,763 | 11/1968 | Capuano | 204/1 F |
| 3,493,484 | 2/1970 | Berg et al. | 422/98 X |
| 3,820,958 | 6/1974 | Cheng et al. | 23/232 E |
| 4,172,705 | 10/1979 | Castro et al. | 422/80 X |
| 4,227,974 | 10/1980 | Peterson et al. | 204/1 F |
| 4,238,198 | 12/1980 | Swaim et al. | 23/232 E X |

FOREIGN PATENT DOCUMENTS 54-151892 11/1979 Japan ................................. 422/83

OTHER PUBLICATIONS

D. L. Noel—Sulfur Compounds in Kraft Pumping Liquor, May 1978—pp. 73-76.
Harry V. Drushel—Trace Sulfur Determination in Petroleum Fractions—1977—pp. 76-81.
B. Ya. Kaplan, T. N. Varavko and I. N. Vladimirskaya—Polarographic Determination of Sulfur by Combustion with Reversible Adsorption of Sulfur Dioxide and Its Reduction to Hydrogen Sulfide—1977—pp. 315-317.
J. J. Renard, G. Kubes, and H. I. Bolker—Polarographic Determination of Sulfur Compounds in Pulping Liquors—1975—pp. 13471352.
John A. Turner, Roger H. Abel, and Robert A. Osteryoung—Normal Pulse Polarographic Analysis Based on Mercury Anodization: Sulfide and Iodide—1975—pp. 1343-1347.
Kaplan, B. Ya; Sevastyanova, T. N.; Shiryaeva, O. A.—Application of Pulse Polarography for the Determination of Trace Amounts of Sulfur—1974—Abstract 32847v, vol. 81 (1974) p. 511.
D. R. Canterford and A. S. Buchanan—Polarographic Behaviour of Sulphide Ion—1973—pp. 193-203.
D. R. Canterford and A. S. Buchanan—Application of Differential Pulse Polarography to Anodic Electrode Processes Involving Mercury Compound Formation—1972—pp. 291-298.
Tamoo Miwa, Yukio Fujii and Atsushi Mizuike—Cathodic Stripping Voltammetry of Sulfide—1971—pp. 475-477.
Dautzenberg, Horst—Continuous Polarographic Detection of Small Amounts of Volatile Material From a Gaseous Mixture. Ger. (East) 73,667—1970.
L. D. Wallace and D. W. Kohlenberger; R. J. Joyce, R. T. Moore, M. E. Riddle, and J. A. McNulty—Comparison of Oxidative and Reductive Methods for the Microcoulometric Determinations of Sulfur in Hydrocarbons—1970—pp. 387-394.
Safwat W. Bishara—Indirect Polarographic Method for the Microdetermination of Sulfur in Organic Compounds—1969—pp. 211-217; Microchemical Journal 15, 211-217 (1970).
Strafelda, Frantisek; Hancil, Vladimir—Polarographic Analyzer for Hydrogen Sulfide in Hydrogen—1966—pp. 143-153.
E. M. Roizenblat, T. I. Fomicheva, and Kh. Z. Brainina—The Determination of Microquantities of Sulfates by the Method of Film Polarography with Accumulation—1966—pp. 799-801.

Primary Examiner—Kenneth M. Schor

[57] ABSTRACT

Method for determining total organic sulfur using reductive pyrolysis and specific electrochemical detection of sulfide ion at a mercury electrode. The method is especially useful for the determination of sulfur in matrices containing halogen or nitrogen compounds. Under routine conditions, a detection limit of less than 50 parts per billion (ppb) can be achieved using differential pulse cathodic stripping voltammetry as the detection mode.

34 Claims, 7 Drawing Figures

Fig. 3

A. toluene blank; B. thianthrene at 0.10 μg S/mL; C. thianthrene at 5.0 μg S/mL; $E_{dep}$ = -0.40 V; injection volume, 40 μL

Effect of deposition potential on sulfide respose conditions: thiophene at 2.82 µg S/mL in methanol solvent; deposition time, 60 seconds stirred, 30 seconds quiet; pulse height, 100mV; scan rate, 5mV/second.

Fig. 6

Effect of deposition time (stirred) on sulfide response. $E_{dep}$=-0.30V; equilibration time (nonstirred), 30 seconds; sulfide concentration, 10 ng/mL.

Fig. 7

REDUCTIVE PYROLYSIS METHOD FOR DETERMINING TRACE SULFUR

FIELD OF THE INVENTION

The invention relates to the analytical field of sulfur analysis, and particularly to an improved method useful for determining trace organic sulfur.

BACKGROUND OF THE INVENTION

Modern chemical technology and environmental concerns have required the determination of sulfur in a variety of matrices down to levels at or below one part per million (ppm). Polymerization inhibitors, catalyst poisoning, and sulfur emissions are especially important areas for sulfur determination. A similar need exists for the ability to rapidly determine trace sulfur in highly halogenated and/or nitrogen containing feedstocks or products.

Although many methods have been developed for the determination of total sulfur at ppm levels, these methods have often been complicated and time consuming. Further, certain constituents in the sample matrix have made some methods impossible to apply.

Among specific prior art methods, the use of combustion-microcoulometry for the determination of sulfur has been widely documented, and systems are commercially available. Both oxidative and reductive pyrolysis with microcoulometric detection have been applied.

In the case of oxidative pyrolysis, the sulfur in the sample matrix is converted to sulfur dioxide ($SO_2$) in an oxygen rich atmosphere at 800° to 1000° C. The $SO_2$ thus formed is trapped in an acidic buffered electrolyte containing a small amount of iodine ($I_2$). The $SO_2$ reacts with iodine to form $SO_3$, while the iodine is reduced to iodide ion ($I^-$). The iodide ion is coulometrically reoxidized to iodine, the amount of charge required being proportional to the original sulfur content of the sample.

Reductive pyrolysis coupled with microcoulometric detection requires that the sulfur be converted to hydrogen sulfide ($H_2S$) in a hydrogen atmosphere at 1100° to 1150° C. The sulfide formed is trapped in a basic electrolyte containing free silver ($Ag^+$) ions. The sulfide entering the cell reduces the silver ion concentration by precipitation of silver sulfide ($Ag_2S$), and the silver ion concentration is reestablished coulometrically.

Both the described coulometric methods are nonspecific, and thus suffer from several interferences. For oxidative pyrolysis, chlorine ($Cl_2$) or bromine ($Br_2$) produced from combustion of halogenated organic materials can replace iodine in the titration step, resulting in an artificially low sulfur assay for the injected sample. Iodine may also be blown out of the titration cell by the pyrolysis gases. Similarly, aldehydes and nitrogen (as NO) can be titrated with iodine to give a positive error. For reductive pyrolysis, halide ions or nitrogen (as HCN) formed during the combustion will precipitate silver ion, giving an artificially high sulfur measurement. Although the solubility product of silver sulfide is much lower than that of silver halides ($10^{-50}$ vs. $10^{-11}$ for AgCl) favoring silver sulfide precipitation, halogen concentrations in excess of ten percent can introduce a significant error in these measurements.

An alternative prior art method for determination of sulfur in halogenated matrices is the reduction of sulfur-containing compounds to sulfide using Raney nickel catalyst. The sulfide can be determined colorimetrically by reaction with methylene blue, or by potentiometric methods. Although both excellent accuracy and precision have been reported, the method requires several hours per determination and sulfur recoveries may vary for different matrices, as is the case for various isomers of dichlorobenzene.

In still another reductive pyrolysis technique recently reported, *Anal. Chem.*, 50, 76 (1978), sulfur compounds are noncatalytically reduced under hydrogen pyrolysis conditions to $H_2S$, which is monitored by photometric measurement of the blackening of a moistened lead acetate-impregnated paper tape. The method is rapid and sensitive but is nonstoichiometric for several common sulfur compounds.

In respect to yet other of the diverse methods developed for measuring sulfur, chemical reduction methods have been proposed, e.g., based on hydriodic acid reduction of sulfur to sulfide with plasma emission detection. These methods are generally satisfactory for inorganic sulfur species, but recoveries are substantially lower for organic species. Replacement of the hydriodic acid reduction apparatus with a reductive pyrolysis system would increase recovery for organic species, but potential hazards due to ignition of hydrogen in the plasma could not be avoided.

Combustion methods, e.g., oxidation flask techniques have also been developed using either x-ray fluorescence detection, thermal conductivity, ion chromatography, potentiometry, polarography or gravimetry for detection. Generally, these methods, however, are applicable only to relatively high sulfur concentrations (i.e., >50 ppm S).

Yet, still other methods which are more sulfur-species specific than the pyrolysis methods discussed, such as those based on gas chromatography with electrolytic conductivity as detection, are more applicable to those matrices which are highly volatile, and thus are restrictively limited in scope of utility.

Accordingly, it is an objective of this invention to provide an improved and broadly applicable method for determining trace sulfur, and which method may be particularly advantageously applied to determine total organic sulfur in diverse matrices.

It is particularly an objective hereof to provide such method which offers all of the combined and important advantages of specific sulfur detection, rapid analysis times, low detection limits, freedom from halogen and nitrogen interferences and solvent effects, and minimal operator attention.

SUMMARY OF THE INVENTION

The invention is an improved method for the determination of sulfur concentration which comprises the steps of reductive pyrolysis of a sulfur-containing sample to produce $H_2S$ sulfur derivative in pyrolysis effluent gas, collection of the $H_2S$ so evolved from the sample in a base electrolyte solution by bubbling the effluent gas through the electrolyte solution, said method producing a concentration of sulfide in electrolyte solution of less than about $2.5 \times 10^{-5}$ M, thereafter detecting the sulfide concentration of the basic electrolyte solution by forming a concentrated sulfide layer on the surface of a mercury electrode in contact with the solution by applying a plating potential to the working electrode vs. a reference electrode, to form a HgS layer on the surface of the working electrode, and thereafter, under conditions of a quiescent solution, scanning the working electrode potential in the cathodic direction to determine as a function of current or a current derivative, total H₂S derivatized sulfur concentration of the analyzed sample.

A further, more specific aspect of the invention relates to the determination of sulfur in an interfering organic matrix comprising, in conjunction with the method described, the further step of bubbling the effluent gas through an aqueous acid solution, which solution is nonoxidative of H₂S, prior to collecting the H₂S in the base electrolyte solution.

Still a further specific aspect of the invention comprises the methods as described, using as the detection mode, differential pulse cathodic stripping voltammetry to obtain a detection limit on the order of 50 parts per billion (ppb) or less sulfur concentration in the analyzed matrix.

THE DRAWING

Yet further objects and advantages of the invention will, in part, be pointed out, and, in part, be apparent from the following detailed description taken together with the accompanying Drawing wherein.

DETAILED DESCRIPTION OF THE INVENTION/PRINCIPLE

The determination of sulfur is in part based on the reduction of typically organic sulfur species to hydrogen sulfide (H₂S), preferably using catalyzed high temperature pyrolysis in a flowing hydrogen stream. Ideally, the balance of the sample matrix is converted to carbon, methane, and water. Halogens (Cl, Br, I=X) are converted to their acid halide forms (HX), while nitrogen species are converted to nitrogen, ammonia and hydrogen cyanide.

The conditions of the experiment require that not more than about $2.5 \times 10^{-5}\,\overline{M}$, and most preferably, not more than about $5 \times 10^{-6}\,\overline{M}$, sulfide is collected from the pyrolysis effluent in a basic electrolyte solution. The conditions are achieved by controlling sample size, and by sample dilution where required.

The determination of sulfide ion is at a working mercury electrode using in sequence (a) plating of the electrode by application of a plating potential ($E_p$) thereto vs. a reference electrode to form an insoluble HgS layer on the surface of the electrode, i.e., "the concentration step", and (b) scanning in the cathodic direction from the plating potential to reduce the deposited HgS. The resulting current or current derivative response is directly proportional to sulfide concentration. Thus, such may be used to accurately determine the derivatized sulfur concentration typically giving the value of total organic sulfur in the analyzed matrix.

The second step (b) is basically a polarographic measurement. As such, it may use any of the polarographic potential scanning wave-forms known to the art, e.g., as described extensively in the text by Bond, *Modern Polarographic Methods in Analytical Chemistry*, Marcel Dekker, Inc., (1980). In this respect, "cathodic scanning voltammetry" is intended to mean a detection mode using steps (a) and (b) with application of any of such known and suitable wave-forms; and the term "differential pulse cathodic stripping voltammetry (DPCSV)" means the more specific form of cathodic scanning voltammetry, which applies a scanning potential in the form of a differential pulse wave-form, e.g., as described in the cited reference (incorporated herein by reference).

In respect to the utility of the method, the novel combination of reductive pyrolysis and detection by cathodic scanning voltammetry offers several inherent advantages for the determination of total organic sulfur. Reductive pyrolysis offers stoichiometric conversion of most sulfur forms to H₂S as compared to oxidative pyrolysis where conversion to SO₂ is typically 80–85%. Sulfides, mercaptans, tetrahydrothiophene 1,1-dioxide, thiophenes, sulfur, sulfoxides, sulfones, organic sulfates and some sulfonates can be completely converted to hydrogen sulfide under pyrolysis conditions. In addition, sulfide detection is specific, e.g., halogens (as HCl, HBr) are electrochemically inactive at potentials where sulfide is detected and consequently, do not interfere as with microcoulometric titration systems. Also the detection is sensitive. The use of differential pulse cathodic stripping voltammetry allows preconcentration of sulfide onto the electrode surface and the detection of low nanogram quantities of sulfide.

PREFERRED APPARATUS AND METHOD CONDITIONS

Figure 1:
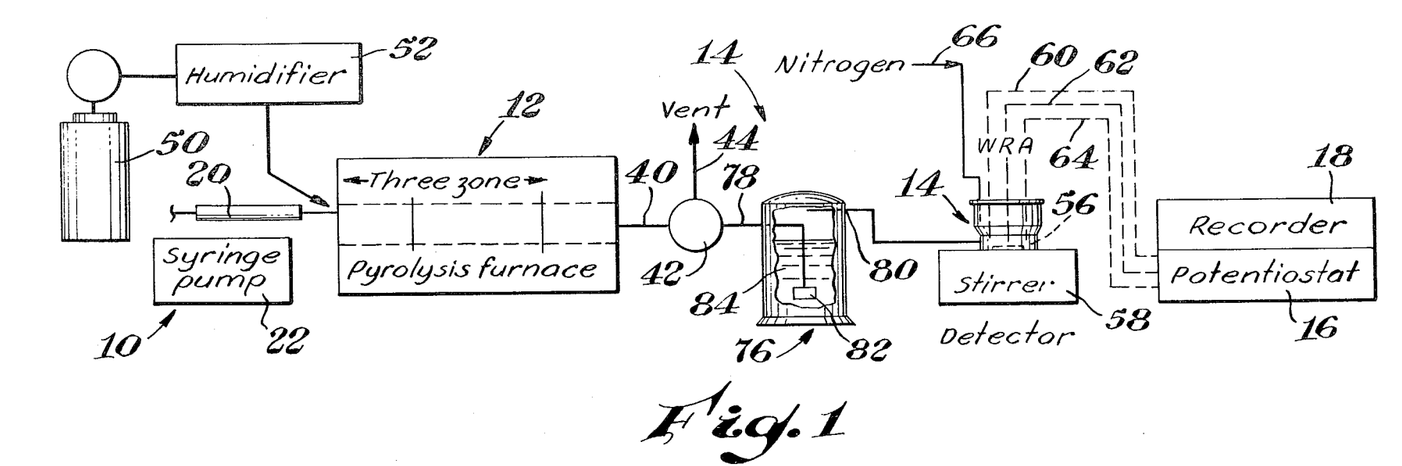
FIG. 1 is an elevational view of a preferred embodiment of apparatus designed for use in practicing the sulfur analysis method of the present invention.

Apparatus for practicing the method of the invention comprises, as illustrated in FIG. 1, a fixed rate sample injector 10, pyrolysis furnace 12, electrochemical cell 14, potentiostat 16 and recorder 18.

In respect to the sample injector 10, sample injections are made using a 50 microliter syringe 20 using a removable three-inch needle (24 gauge). Injected sample volume is preferably about 40 μl. The syringe plunger is advanced at a controlled rate using, e.g., a Sage Model 351 syringe pump 22. The pump allows the selection of a wide range of injection rates. Typical injection rates are between 0.20 to 0.25 microliters per second.

The pyrolysis furnace is preferably a Dohrmann-Envirotech Model S-300 furnace equipped with three separately controlled heating zones. The temperature of each zone is monitored by a 10% ruthenium-90% platinum/platinum thermocouple. This commercial furnace is also equipped with separately regulated gas flow meters for the flow regulation of reactant (humidified hydrogen), and purge (argon or nitrogen) gases.

Figure 2:
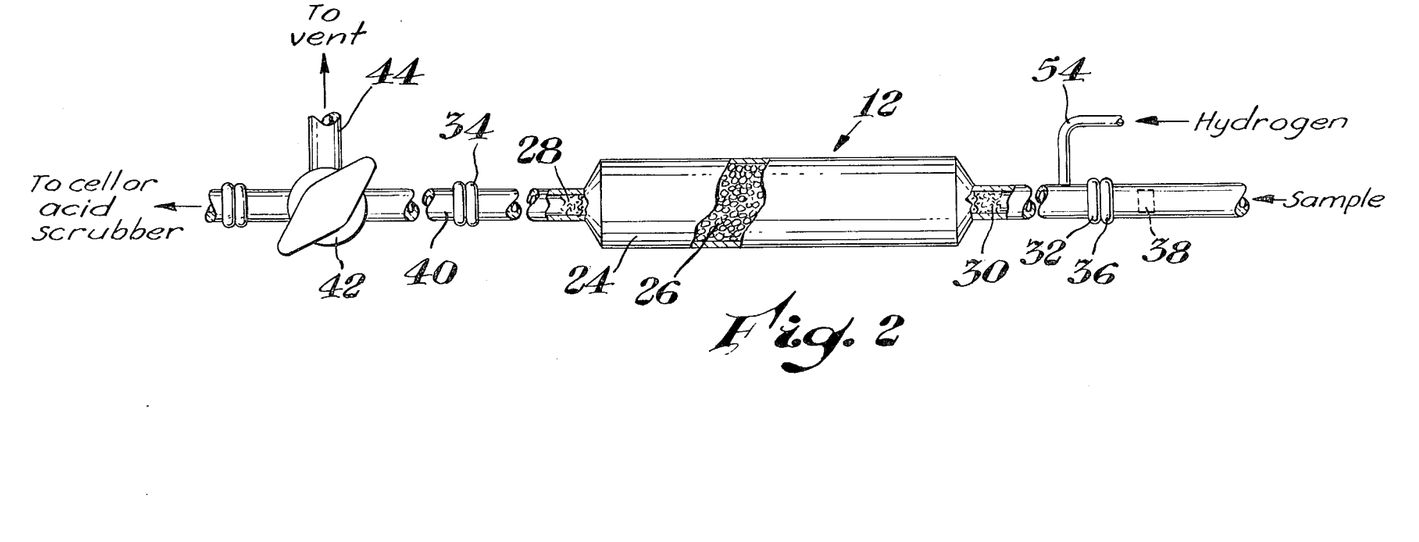
FIG. 2 is an enlarged partial view of the apparatus of FIG. 1, illustrating the detail of the pyrolysis furnace.

FIG. 2 illustrates, in more detail, the preferred structure of the pyrolysis furnace which comprises a quartz pyrolysis tube 24, the center section of which is packed with a granular 10% platinum on alundum (Al₂O₃) catalyst bed 26. Alternatively, other forms of catalyst which may be used in the practice of the invention include palladium, ruthenium, rhodium, and the like, such as described in more detail in the text by Thomas, *Catalytic Processes and Proven Catalysts*, Academic Press, (1970).

The catalyst bed is held in place with plugs 28, 30 fashioned, e.g., from platinum screen. Both ends of the quartz tube 24 are fitted with 18/9 male ball joints, 32, 34. The inlet side accepts a 18/9 female ball joint 36 fitted with a silicon rubber septum 38 through which is injected sample. The outlet side accepts a glass tee 40 fitted with a manual three-way stopcock 42 of all Teflon ® construction, and which is used to direct gas flow from the pyrolysis tube to either the electrochemical cell 14 or a vent 44.

Alternately, the manual switching system may be replaced by an automated valve, e.g., a Fluorocarbon SPC 124-3B three-way valve of all Teflon ® construction operated by a Whitey MS-131DA pneumatic actuator. In this embodiment, the actuator is driven in both directions by argon at 25 psi pressure, the argon flow direction being controlled by a four-way electrically-actuated solenoid valve, in turn actuated by a switched 110 volt AC outlet using a Lindberg Enterprises Chrontrol DL-4 relay-equipped timer.

Hydrogen reactant gas from a compressed gas supply source 50 is bubbled through a 250 milliliter gas scrubbing tower or humidifier 52 filled with deionized water and admitted to the pyrolysis tube 24 through a side arm 54 (shown in FIG. 2). The humidifier is enclosed in a housing constructed of ¼-inch Plexiglas ® to contain glass fragments in case of flashback. The side arm 54 forming the hydrogen entry point, and the sample entry through septum 38 are positioned in the first of three heated zones of the pyrolysis tube. Typical furnace zone operating temperatures are 700° C. for the inlet zone, 1100° C. for the center catalyst zone, and 850° C. for the outlet zone. A standby temperature of 900°–950° C. (catalyst zone only) is used to reduce the devitrification rate of the pyrolysis tube.

In addition to its use as the hydrogen inlet, side arm 54 is also connected by a valve connection to an inert gas supply (e.g., argon or nitrogen), and an oxygen gas supply for periodically reconditioning the pyrolysis tube and catalyst bed. The inert gas supply is used, e.g., at all times prior to opening the apparatus to air to displace possible explosive hydrogen. In addition, an oxygen supply is needed to periodically recondition the pyrolysis tube to oxidize coke formed on the catalyst. The system following reconditioning is purged overnight with argon (approximately 100 cc/minute) before the hydrogen flow is reestablished for further analysis.

Referring to the electrochemical cell 14, the cell contains a magnetic stirring bar 56, and is supported on a magnetic stirring unit 58. Cell 14 comprises basically a mercury working electrode 60, reference electrode 62, and optional auxiliary electrode 64. Additionally, the cell is purged through a nitrogen inlet tube 66 to deoxygenate the cell prior to each determination. A preferred electrode system is, for example, an EG & G Princeton Applied Research (PARC) Model 303 Static Mercury Drop Electrode (SMDE), controlled by a PARC Model 174A potentiostat 16. The porous glass frit of the Model 303 SMDE reference compartment, designated as element 62a, is preferably replaced by a microporous polyethylene frit obtained from PARC. This frit has a somewhat higher leak rate than porous glass, but lasts much longer in basic electrolytes. The reference filling solution is preferably 0.30 $\overline{M}$ calcium chloride (noncritical) saturated with silver ion to form a silver/silver chloride reference.

The working and reference electrodes described, while suited to the practice of the invention are not intended to limit the scope of the invention. Thus, essentially any mercury electrode form known in the art may be used. Alternative mercury and reference electrodes suited for use in the invention are described, e.g., by Vydra et al., *Electrochemical Stripping Analysis*, Ellis Horwood Limited (1976), incorporated herein by reference.

Figure 3:
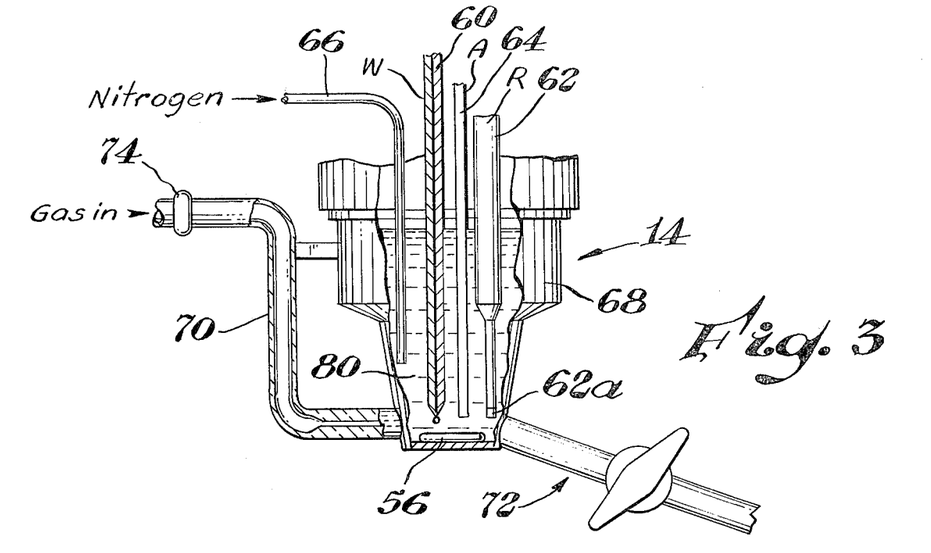
FIG. 3 is a view like FIG. 2, only illustrating the detail of a preferred detector design for use with the FIG. 1 apparatus.

The preferred detector cell or cell body is of a modified design, suited to the purposes of the invention, and is shown separately in FIG. 3. It comprises a Model 303 cell body 68 modified by the addition of a side-arm bubbler 70 and a drain 72. The inlet end of the side-arm bubbler is fitted with a 12/5 female ball joint 74 which is connected to the outlet end of the glass tee 40 (or alternatively, to an acid scrubbing tower as described below). The end of the side-arm bubbler 70 which protrudes into the cell is drawn down to a capillary of less than about 0.5 millimeter, and most preferably, about 0.2–0.3 millimeter in diameter. The drain 72 allows easy rinsing and refilling of the cell after each analysis. The side-arm bubbler and glass tee 40 are wrapped with heater tapes (not shown) to prevent condensation and sulfide carryover from analysis to analysis.

The base electrolyte solution 86 of cell body 68 is most preferably 0.20 $\overline{M}$ lithium hydroxide (LiOH) prepared from lithium hydroxide monohydrate (Baker Analyzed Reagent) with 0.02% (w/w) ethylenediaminetetraacetic acid (EDTA-Polarographic Grade, Southwestern Analytical Chemicals) in deionized water.

Among other base electrolytes which may be beneficially used are those having low trace metal contamination, achieved by way of complexing additives or otherwise, and selected from the group of nonprecipitating metal and ammonium hydroxides and soluble amines, added to a suitable polar solvent, e.g., deionized water, to produce a concentration of preferably not greater than about 0.4 $\overline{M}$ electrolyte. Particularly in the case of halogenated sample matrices, ionic strength ($\mu$) of the electrolyte solution, following $H_2S$ collection, should not be allowed to exceed about 1, and most preferably is lower than about 0.5 for trace analysis.

Apparatus which is not used in all cases, but which is necessary for the purposes of certain analyses due to matrix interferences, is the use of an acid scrubbing step, such as by use of the scrubbing tower 76 illustrated in FIG. 1. The tower 76 includes an inlet arm 78, fitted with a male ball joint, and outlet arm 80 fitted with a female ball joint, each for connection in line between stopcock 42 and side arm bubbler 70 of the electrochemical cell. All such connections are preferably made using a pressure clamp and grease seal between the mating ball joint surfaces. The inlet arm 80 terminates in a glass frit 82 which produces a fine dispersion of gas bubbles in acidic scrubbing solution 84 contained in the scrubbing tower. The scrubbing solution may suitably comprise about 20 ml of aqueous 0.1 $\overline{M}$ $HClO_4$. In some cases, deionized water, pH about 5.5, may be suitably substituted as well as other acids such as HCl, $H_2SO_4$, $H_3PO_4$, etc. Acids which oxidize $H_2S$, such as $HNO_3$, are not suitably employed in the scrubbing tower.

OPERATION

A typical analysis cycle requires about 15 minutes. The detector cell is rinsed once with 0.1 M $HNO_3$ and twice with deionized water, and filled with 10 mL of electrolyte, which is then deoxygenated with Matheson prepurified nitrogen for four minutes. The sample syringe is filled with 40 $\mu$l of solution, the plunger withdrawn to 45 $\mu$l, and the sample (40 $\mu$l) injected into the furnace tube at a controlled rate of 0.20 or 0.25 $\mu$l per second.

After the syringe is emptied, the furnace is purged an additional 40 seconds to completely displace sulfides from the furnace tube. Gases from the pyrolysis tube are then diverted to the vent and the contents of the detector cell analyzed following an additional one minute nitrogen purge.

Typical parameters for analysis are: furnace inlet temperature, 700°–900° C. (temperature dependent on sample composition); center temperature, 1100° C.; outlet temperature, 850° C. Using differential pulse cathodic stripping for detection, typical analytical parameters (DPCSV) are: $E_{dep} = -0.30$ V; deposition time, 60 seconds, stirred; equilibration time, 30 seconds, unstirred; scan rate, 5 mV per second; drop time, 1.0 second; pulse height, 100 mV. Unless otherwise noted, these conditions are used for all data reported in the Examples below.

EXAMPLE 1—RESPONSE CHARACTERISTICS

Figure 4:
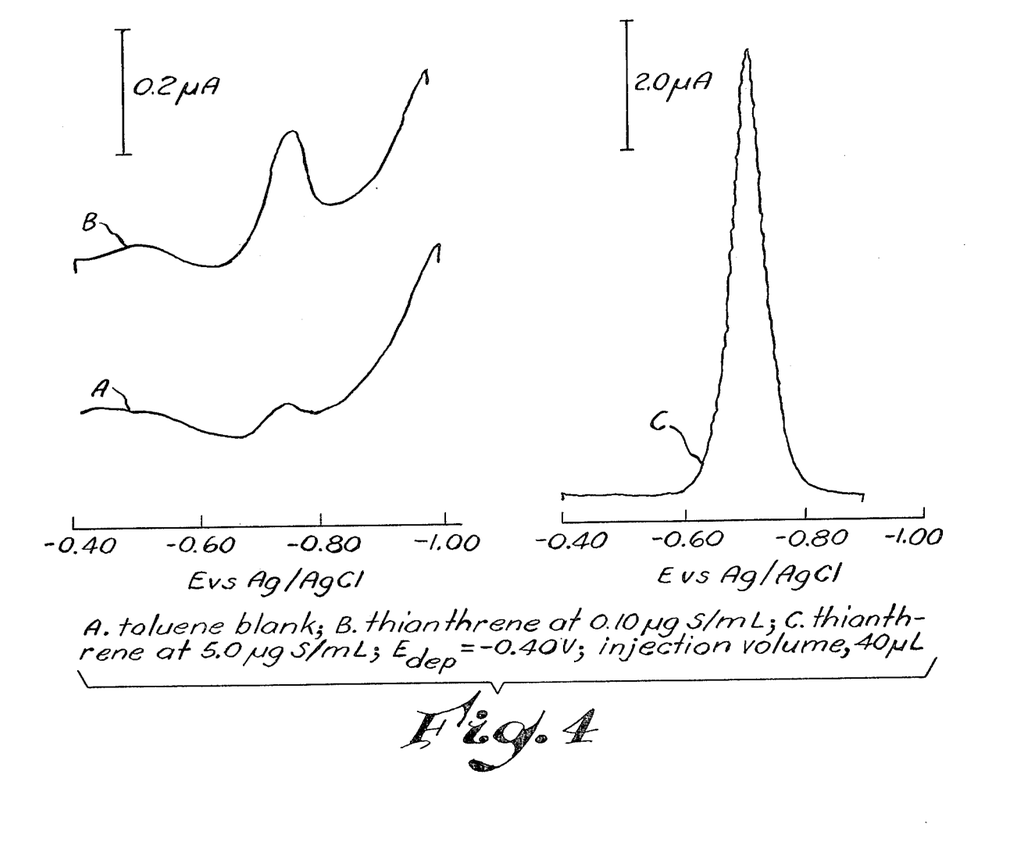
FIGS. 4–7 are reproductions of various graphs and current response curves developed using the method of the invention, and are associated with certain of the working Examples 1–14, below.

Typical responses for a toluene solvent blank (containing sulfur), and standards of 0.1 µg S/mL and 5.0 µg S/mL are shown in FIG. 4 using DPCSV as the detection mode. Based on a limit of 2.5 times the blank response, a detection limit of 0.05 µg S/mL is calculated for an injection volume of 40 µL. The detection limit can be further decreased with optimization of detection conditions, i.e., by increasing the deposition time, by increasing the stirring rate, and by using multiple or larger sample injection volumes.

EXAMPLE 2—CALIBRATION

Figure 5:
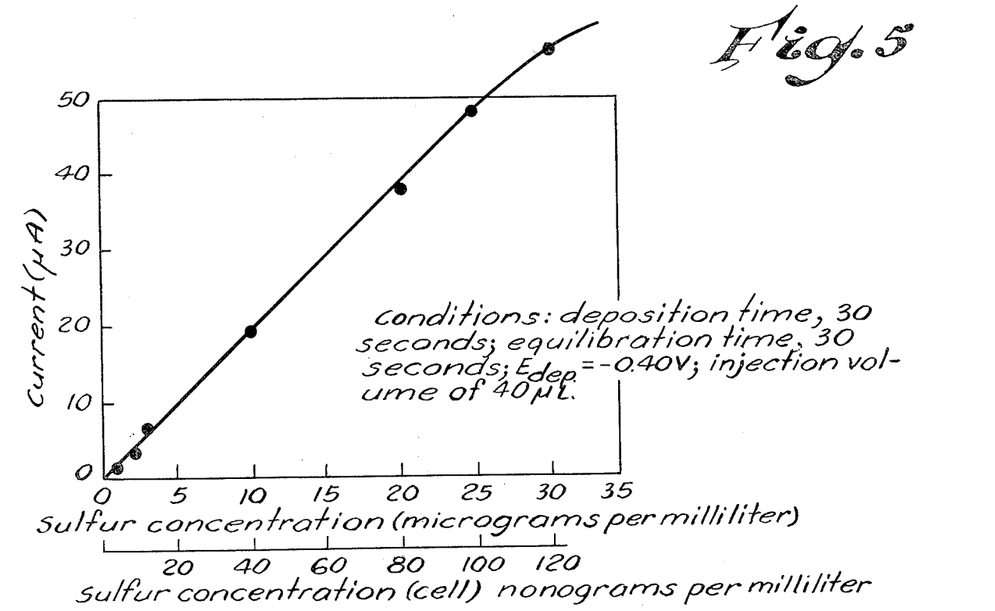

The calibration for sulfur determination in toluene is shown in FIG. 5. The calibration is given as to both the sulfur concentration in the sample being injected and the sulfide concentration which is being detected in the cell assuming a 40 µL sample injection. Using DPCSV, the response is linear to about 30 µg S/mL for an injected sample.

EXAMPLE 3—CURRENT RANGE SELECTION

Under DPCSV detection conditions, a significant decrease in peak height (~10–15%) is observed on successive scans of the same solution. Apparently, a small fraction of the sulfide concentration in the bulk solution is depleted during the deposition process. The effect is not observed using differential pulse polarography (DPP) as the detection mode. When analyzing an unknown, it is thus preferred to first perform a DPP analysis of the solution. The measured peak height, allowing for about a 25-fold increase in signal for DPCSV, is beneficially used to determine the appropriate potentiostat current range selection for the DPCSV analysis mode, e.g., in the case of an unknown sample.

EXAMPLE 4—REPEATABILITY

The repeatability of the method is tested by analyzing a monochlorobenzene solution on two successive days using DPCSV as the detection mode. The data is given in Table I.

TABLE I

Repeatability of Total Sulfur Determination In Monochlorobenzene Using Differential Pulse Cathodic Stripping Voltammetry

| $n_i$ | $x_i$ (ppm S) |
|---|---|
| 1 | 0.70 |
| 2 | 0.64 |
| 3 | 0.64 |
| 4 | 0.68 |
| 5 | 0.66 |
| 6 | 0.73 |
| 7 | 0.62 |
| 8 | 0.64 |
| 9 | 0.61 |
| 10 | 0.69 |
| 11 | 0.63 |

$\bar{x} = 0.66$
$\sigma = 0.037$

Relative precision at 95% confidence $= \frac{2\sigma}{\bar{x}} \times 100 = \pm 11.4\%$

EXAMPLE 5—PYROLYSIS CONDITIONS

Catalyst temperature. The effect of catalyst temperature on sulfur recovery from selected sulfur compounds is shown in Table II.

TABLE II

Effect of Furnace Center Temperature On Conversion of Sulfur Compounds to $H_2S$; Concentration, 2 µg S/mL; Injection Volume, 40 µL; Furnace Inlet, 710° C.

| Compound | Solvent | Percent Conversion at 1050° C. | 1150° C. |
|---|---|---|---|
| Thiophene | Methanol | 99 | — |
| Thiophene | Carbon Tetrachloride | 98 | 97 |
| Tetrahydrothiophene 1,1-dioxide | Water | 98 | 84 |
| Tetrahydrothiophene 1,1-dioxide | Methanol | 99 | — |
| Dimethylsulfoxide | Methanol | 105 | 87 |
| Thianthrene | Methanol | 104 | 83 |
| Isooctylthioglycolate | Methanol | 98 | — |
| Thiourea | Water | 100 | 93 |
| Thiocarbanilide | Methanol | 9 | — |
| Benzenesulfonic acid | Methanol | 9 | 9 |
| Dibutyl sulfide | Methanol | 99 | — |

The sulfur compounds reported in the data of Table II are representative of classes of compounds which are encountered in a typical analysis. At 1050° C., the recoveries of most of these species are near 100%. By increasing the center furnace temperature to 1150° C., however, sulfur recovery is actually lowered in most cases. The low recoveries for sulfonate and thiocarbonalide are most likely due to the low volatilities of these compounds at 700° C. Recoveries are calculated based on the response of a calibrated $Na_2S$ standard spiked directly into the detector cell.

Repetitive injections of standards prepared in toluene or isooctane tended to give steadily decreasing responses over the span of a day, when using a center furnace temperature of 1050° C.

Visual inspection of the pyrolysis tube catalyst bed indicated a buildup of coke on the surface of the catalyst. By increasing the center temperature to 1090°–1100° C., repeatability is improved and coking reduced. Recoveries for sulfur species examined at 1100° C. are found identical to those at 1050° C. At 1100° C., however, the quartz pyrolysis tube slowly devitrifies and the lifetime of the tube is typically only 3–4 weeks. The lifetime of the tube can be increased to at least two months when the tube wall thickness is increased to 2.5 mm.

EXAMPLE 6—HYDROGEN FLOW RATE

The sulfide peak current as a function of hydrogen flow rate is studied in this Example. Data produced show the flow rate has little effect on peak current in the range of 100–300 cc/minute, but a small maximum occurs at 200 cc/minute. At this flow rate, the residence time in the pyrolysis tube is approximately twelve seconds.

EXAMPLE 7—INJECTION RATE

The rate of sample injection is studied, and found to show little effect on response. At injection rates of 0.10–1.0 μL/sec., the peak current varied by less than 5 percent. However, at injection rates $\geq 0.4$ μL/sec., a yellow-brown film condenses on the walls of the glass tubing connecting the pyrolysis tube to the electrochemical cell. After several injections, the film blocks the capillary to the cell. Presumably, the film is due to the incomplete pyrolysis of hydrocarbons.

At injection rates of 0.20–0.30 μL/sec., little, if any, filming is observed even after several days of continued use, as long as the valve and tubing at the pyrolysis tube outlet are heated (~80° C.).

EXAMPLE 8—DEPOSITION CONDITIONS

Figure 6:
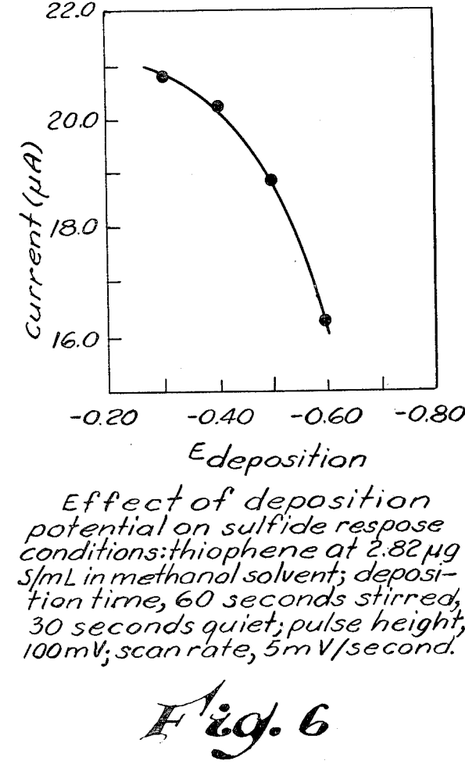

To achieve high sensitivity for total sulfur measurement, the differential pulse cathodic stripping response for sulfide is studied. The effect of deposition potential on response is shown in FIG. 6. The maximum response is obtained when using a deposition potential of −0.30 V.

Figure 7:
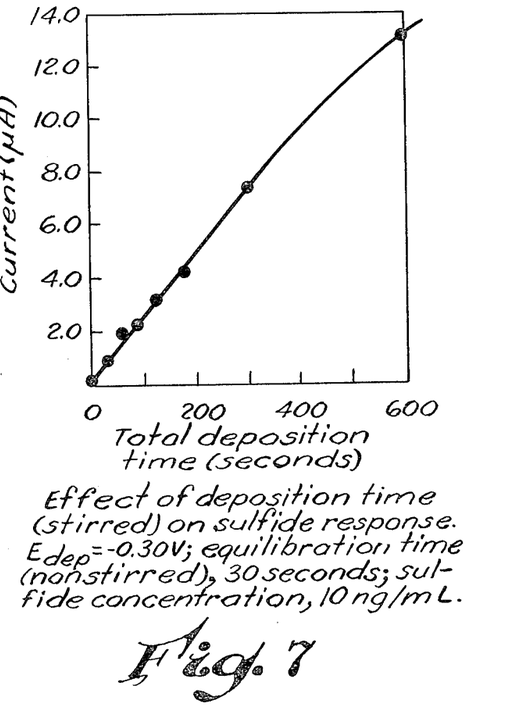

The effect of deposition time on response is also studied and the results shown in FIG. 7. The peak current increases linearly with deposition times up to about 300 seconds, above which the current dependence is nonlinear, probably due to multilayer coverage of the electrode surface. Typically, a deposition time of 30 to 60 seconds (stirred) and an equilibration time (unstirred) of 30 seconds is used.

EXAMPLE 9—Electrolyte Composition

Obtaining a low blank response for a supporting electrolyte containing only an alkali metal hydroxide such as KOH or NaOH is difficult since these reagents also contain trace concentrations of heavy metals (i.e., lead). The peak current for lead in basic electrolyte occurs at −0.60 V and is convoluted with that of sulfide. Because of generally lower trace metal concentrations, lithium hydroxide is the reagent of choice for the preparation of the supporting electrolyte.

To further minimize trace metal effects, ethylenediaminetetraacetic acid (EDTA, 0.02% w/w) is added to the supporting electrolyte. The addition of EDTA lowers the sulfide response by about 10 percent relative to that in electrolyte containing no EDTA. However, background response is significantly improved, apparently due to the complexing properties of EDTA. The effect of EDTA on sulfide response (5 μg/mL) with lead (1 μg/mL) present as a trace contaminant is also studied. Without EDTA, the presence of lead made accurate quantitation of the sulfide impossible. With EDTA, the lead response is completely eliminated, and the observed sulfide response is identical to that of sulfide without lead present. Lead concentrations up to 5 μg/mL could be tolerated in the electrolyte before the sulfide response is affected.

To determine sulfur in a halogen matrix, the electrolyte additionally must contain sufficient alkalinity to be in excess of the HX produced from the pyrolysis. For example, pyrolysis of 40 μL of carbon tetrachloride will produce $1.65 \times 10^{-3}$ moles of HCl. Assuming a 10 mL cell volume, at electrolyte concentrations less than about 0.17 M LiOH, the HCl produced will consume the basic capacity of the electrolyte and sulfide will be liberated from solution. An electrolyte concentration of 0.20–0.25 M LiOH was therefore used for most determinations. No advantage was observed for increasing the hydroxide concentration beyond 0.25 M. In fact, at concentrations >0.30 M the sulfide response is suppressed, probably due to the higher solution viscosity.

EXAMPLE 10—EFFECT OF SAMPLE MATRIX ON SULFUR RESPONSE (AROMATICS)

Ideally, an analytical technique for total sulfur determination should be free of matrix effects. The effect of several solvents on sulfur response is tested using standard solutions of thianthrene and dimethylsulfoxide. The data is illustrated in Tables III and IV:

TABLE III

Effect of Solvent on Sulfur Determination - Thianthrene at 2.5 μg S/mL, Furnace Inlet 710° C. Detection, Differential Pulse Cathodic Stripping Voltammetry at $E_{dep} = -0.30$ V

| Solvent | Net Peak Current (μA) |
|---|---|
| Acetone | 6.25 |
| Methanol | 6.30 |
| Butanol | 6.46 |
| Tetrahydrofuran | 6.46 |
| Isooctane | 6.22 |
| Heptane | 6.22 |
| Toluene | 5.00 |
| Toluene[a] | 6.20 |

[a]Using a 0.1 M̄ HClO₄ scrubber tower between the furnace outlet and the detection cell.

TABLE IV

Effect of Solvent on Sulfur Determination - Dimethyl Sulfoxide at 2.2 μg S/mL, Furnace Inlet, 710° C.; Detection, Differential Pulse Cathodic Stripping Voltammetry at $E_{dep} = 0.40$ V

| Solvent | Net Peak Current (μA) |
|---|---|
| Methanol | 2.92 |
| Water | 2.96 |
| Carbon Tetrachloride | 2.96 |
| Benzyl Alcohol | 2.19 |

Generally, interpreting the data of the above tables, it may be concluded that typical solvents have little, if any, effect on sulfur response. Aromatic solvents, however, suppress the sulfur response by about 20%. By installing the acid scrubbing tower between the furnace outlet and the cell inlet, the sulfur response, however, is restored to its original value. Presumably, the combustion products of these aromatics are less volatile and compete with sulfide for the electrode surface via adsorption when present in the detection cell. For sulfur determination in an aromatic matrix or an unknown matrix, the use of standard addition techniques and/or the use of the acidic scrubbing tower is preferred.

EXAMPLE 11—Chlorine Matrix Effects

Because of its electrochemical inactivity, chlorine (as HCl) is not expected to affect sulfide determination. This hypothesis is confirmed for carbon tetrachloride. The effect of chlorine was further tested by fortifying mono- and dichlorobenzene with known concentrations of thianthrene and determining sulfur recovery. Each recovery was calculated based on the response of an external standard in toluene solvent. From the data as shown in Table V, recovery is complete.

TABLE V

Recovery of Sulfur From Fortified Mono- and Dichlorobenzene Detection, Differential Pulse Cathodic Stripping Voltammetry at $E_{dep} = -0.30$ V; Furnace Inlet, 710° C.; Test Solution, Thianthrene in Toluene

| Sulfur Concentration ($\mu g/mL$) | | Percent Recovery |
|---|---|---|
| Added | Found | |
| 0.63 | 0.61 | 97 |
| 0.31 | 0.32 | 103 |
| 0.62 | 0.57 | 92 |
| 2.00 | 2.1 | 105 |
| 1.00 | 0.96 | 96 |
| 0.26 | 0.20 | 80 |
| 0.20 | 0.22 | 110 |
| 1.50 | 1.6 | 107 |
| 0.20 | 0.19 | 95 |
| 0.40 | 0.43 | 108 |
| 1.23 | 1.6 | 128 |
| 0.15 | 0.18 | 122 |
| 1.59 | 1.8 | 112 |

EXAMPLE 12—Bromine Matrix Effects

The effect of bromine (as HBr) on sulfur determination is also tested by determining the recovery of sulfur from bromoethane which is fortified with known concentrations of thianthrene. Each recovery is calculated based on the response of an external standard in methanol solvent. The data obtained is equivalent to that shown in Table V, showing recovery is complete.

EXAMPLE 13—Nitrogen Matrix Effects

Under conditions of reductive pyrolysis, nitrogen-containing compounds in the sample are typically converted to nitrogen, ammonia, and hydrogen cyanide. Neither nitrogen or ammonia is electrochemically active at the mercury electrode; however, cyanide reacts with mercury to give an anodic wave at $E_{\frac{1}{2}}$ $Hg(CN)_2 = -0.36$ V vs SCE. Since sulfide deposition for cathodic stripping measurements is typically performed at $E = -0.30$ V vs. Ag/AgCl, one might expect cyanide to have an effect on the sulfide measurement.

The effect is tested using standard sulfur solutions containing acetonitrile and methanol. At a deposition potential of $E = -0.30$ V, sulfide can be determined in solutions containing up to 25% acetonitrile (v/v) when using standard addition techniques. Standard addition is required because the sulfide response is suppressed relative to the response in methanol alone.

The effect of cyanide is minimized by using a more cathodic deposition potential. At $E_{dep} = -0.50$ V, equivalent sulfide response is observed for a 2.8 $\mu g$ S/mL standard in the presence and absence of 0.2% acetonitrile. The loss of sulfide sensitivity because of the more cathodic deposition potential is only slight (−11%) as shown previously in FIG. 6.

The effect of nitrogen concentration (as N/S mole ratio) on sulfide response is also studied. No effect is observed until N/S exceeds about 500. At a N/S~1000, the error for direct sulfide measurement is about −11%. Since calibration curves are linear even at relatively high nitrogen concentrations, sulfide is best quantitated by standard addition techniques for N/S>500.

EXAMPLE 14—Catalyst Conditioning

Prior to the determination of sulfur in a halogen-containing matrix, the catalyst is preferably conditioned by injection of several 40 $\mu L$ aliquots of carbon tetrachloride or sample, usually without trapping of the resultant pyrolysis gases. With conditioning, a reliable result can be obtained on the first injection. Apparently, under pyrolysis, the halogen matrix establishes a new equilibrium with the catalyst surface and some sulfide is displaced from the catalyst bed.

What is claimed is:

1. An improved method for the determination of sulfur concentration which comprises the steps of reductive pyrolysis of a sulfur-containing liquid sample to produce $H_2S$ sulfur derivative in pyrolysis effluent gas, in-line collection of the $H_2S$ so evolved from the sample in a base electrolyte solution by bubbling the effluent gas through the electrolyte solution, said method producing a concentration of sulfide in electrolyte solution of less than about $2.5 \times 10^{-5}$ molar, thereafter detecting the sulfide concentration of the base electrolyte solution by forming a concentrated sulfide layer on the surface of a mercury working electrode in contact with the solution by applying a plating potential to the working electrode vs. a reference electrode, to form a HgS layer on the surface of the working electrode, and thereafter, under conditions of a quiescent solution, scanning the working electrode potential in the cathodic direction to determine as a function of current or a current derivative, total $H_2S$ derivatized sulfur concentration of the analyzed sample.

2. The method of claim 1 wherein the effluent gas is added to the electrolyte solution through a heated capillary.

3. The method of claim 2 using a capillary of not greater than about 0.5 mm in diameter.

4. The method of claim 3 using a heated capillary of between about 0.2–0.3 mm in diameter.

5. The method of claim 1 comprising the step of bubbling the effluent gas through an aqueous acid solution prior to collecting the $H_2S$ in the base electrolyte solution.

6. The method of claim 5 using as the acid scrubbing solution, one or more of the group of aqueous $HClO_4$, $H_3PO_4$, $HCl$ or $H_2SO_4$.

7. The method of claim 5 using as the acidic scrubbing solution deionized water.

8. The method of claim 5 using the step of adding the scrubbed effluent gas to the base electrolyte solution through a heated capillary of not greater than about 0.5 mm in diameter.

9. The method of claim 8 using for the addition of the scrubbed effluent gas to the electrolyte solution, a heated capillary of between about 0.2–0.3 mm in diameter.

10. The method of claim 1 using as the electrolyte solution deionized water, to which is added not greater than about 0.4 molar base electrolyte.

11. The method of claim 10 wherein the base electrolyte comprises a non-precipitating metal or ammonium hydroxide or an aqueous solution of an amine.

12. The method of claim 10 wherein the supporting electrolyte solution contains a trace metal complexing additive.

13. The method of claim 10 wherein the supporting electrolyte solution comprises LiOH to which is added, as a complexing additive, ethylenediaminetetraacetic acid.

14. The method of claim 10 wherein the effluent gas is added to the electrolyte solution through a heated capillary of not greater than about 0.5 mm in diameter.

15. The method of claim 14 using a heated capillary of between about 0.2–0.3 mm in diameter.

16. The method of claim 10 comprising the step of bubbling the effluent gas through an aqueous acid solution prior to collecting the $H_2S$ in the base electrolyte solution.

17. The method of claim 16 using as the acid scrubbing solution, one or more of the group of aqueous $HClO_4$, $H_3PO_4$, $HCl$ or $H_2SO_4$.

18. The method of claim 16 using as the acidic scrubbing solution deionized water.

19. The method of claim 16 using the step of adding the scrubbed effluent gas to the base electrolyte solution through a heated capillary of not greater than about 0.5 mm in diameter.

20. The method of claim 19 using for the addition of the scrubbed effluent gas to the electrolyte solution, a heated capillary of between about 0.2–0.3 mm in diameter.

21. The method of claim 1 wherein said method produces a concentration of sulfide in electrolyte solution of less than about $5 \times 10^{-6}$ molar.

22. The method of claim 21 wherein the effluent gas is added to the electrolyte solution through a heated capillary of not greater than about 0.5 mm in diameter.

23. The method of claim 22 using a heated capillary of between about 0.2–0.3 mm in diameter.

24. The method of claim 21 comprising the step of bubbling the effluent gas through an aqueous acid solution prior to collecting the $H_2S$ in the base electrolyte solution.

25. The method of claim 24 using as the acid scrubbing solution, one or more of the group of aqueous $HClO_4$, $H_3PO_4$, $HCl$ or $H_2SO_4$.

26. The method of claim 24 using as the acidic scrubbing solution deionized water.

27. The method of claim 24 using the step of adding the scrubbed effluent gas to the base electrolyte solution through a heated capillary of not greater than about 0.5 mm in diameter.

28. The method of claim 27 using for the addition of the scrubbed effluent gas to the electrolyte solution, a heated capillary of between about 0.2–0.3 mm in diameter.

29. The method of claim 28 using as the electrolyte solution deionized water, to which is added not greater than about 0.4 molar base electrolyte.

30. The method of claim 29 wherein the base electrolyte comprises a non-precipitating metal ammonium hydroxide or an aqueous solution of an amine.

31. The method of claim 30 wherein the supporting electrolyte solution contains a trace metal complexing additive.

32. The method of claim 29 wherein the supporting electrolyte solution comprises LiOH to which is added, as the complexing additive, ethylenediamine tetraacetic acid.

33. The method of claim 29 wherein the ionic strength $\mu$ of the electrolyte solution, following collection of the $H_2S$, does not exceed about 0.5.

34. The method of claim 33 wherein the sample comprises halogenated compounds.

* * * * *

UNITED STATES PATENT AND TRADEMARK OFFICE
CERTIFICATE OF CORRECTION

PATENT NO. : 4,330,298
DATED : May 18, 1982
INVENTOR(S) : David D. Hawn; Robert E. Reim It is certified that error appears in the above—identified patent and that said Letters Patent is hereby corrected as shown below:

Sheet 3 of the Drawings, last line under Fig. 5, delete "nonograms" and insert therefor --nanograms--.

Sheet 3 of the Drawings, under Fig. 6, delete "respose" and insert --response--.

On the cover page, first column, under "Other Publications", J. J. Renard et al., last line, delete "pp. 13471352" and insert --pp. 1347-1352--.

Col. 6, line 61, delete "0.1 M" and insert therefor --0.1 $\overline{M}$--.

Signed and Sealed this

Third Day of June 1986

[SEAL]

Attest:

DONALD J. QUIGG

Attesting Officer

Commissioner of Patents and Trademarks